US00PP19250P2

(12) United States Plant Patent
Kleinhanns

(10) Patent No.: US PP19,250 P2
(45) Date of Patent: Sep. 23, 2008

(54) ***OSTEOSPERMUM* PLANT NAMED 'ASTRA SNOWWHITE'**

(50) Latin Name: *Osteospermum hybrida*
Varietal Denomination: Astra Snowwhite

(75) Inventor: Christoph E. Kleinhanns, Gernrode (DE)

(73) Assignee: Hamer Bloemzaden B.V., H.I. Ambacht (NL)

( * ) Notice: Subject to any disclaimer, the term of this patent is extended or adjusted under 35 U.S.C. 154(b) by 0 days.

(21) Appl. No.: 11/827,279

(22) Filed: Jul. 11, 2007

(51) Int. Cl.
*A01H 5/00* (2006.01)

(52) U.S. Cl. ..... Plt./360

(58) Field of Classification Search ..... Plt./360
See application file for complete search history.

(56) References Cited

U.S. PATENT DOCUMENTS

| | | | | | |
|---|---|---|---|---|---|
| PP10,596 | P | * | 9/1998 | Kanno | Plt./360 |
| PP16,896 | P2 | * | 7/2006 | Kawashima | Plt./360 |
| PP17,419 | P2 | * | 2/2007 | Larsen | Plt./360 |
| 2006/0179536 | P1 | * | 8/2006 | Kawashima | Plt./360 |

* cited by examiner

*Primary Examiner*—Wendy C. Haas
(74) *Attorney, Agent, or Firm*—Jondle & Associates, P.C.

(57) ABSTRACT

An *Osteospermum* cultivar particularly distinguished by small, bright white flowers, early flowering, good garden performance in the summer and a compact plant habit is disclosed.

1 Drawing Sheet

Genus and species: *Osteospermum hybrida.*
Variety denomination: 'Astra Snowwhite'.

BACKGROUND OF THE NEW PLANT

The present invention comprises a new and distinct cultivar of *osteospermum,* botanically known as *Osteospermum hybrida,* and hereinafter referred to by the cultivar name 'Astra Snowwhite'. 'Astra Snowwhite' originated from crossbreeding in March 2003 in Quedlinburg, Germany. The female parent was an *osteospermum* plant with white flowers. The male parent was an *osteospermum* plant with cream flowers.

The new cultivar was first propagated in summer of 2006 from mother stock and has been asexually reproduced through vegetative cuttings for four generations. The present invention has been found to retain its distinctive characteristics.

SUMMARY OF THE INVENTION

The following are the most outstanding and distinguishing characteristics of this new cultivar when grown under normal horticultural practices in Quedlinburg, Germany.

1. Small bright white flowers;
2. Early flowering;
3. Good garden performance during the summer; and
4. Compact plant habit.

DESCRIPTION OF THE PHOTOGRAPH

This new *Osteospermum* plant is illustrated by the accompanying photograph which shows the overall plant habit, including blooms, buds and foliage of the plant in full color, the colors shown being as true as can be reasonably obtained by conventional photographic procedures.

DESCRIPTION OF THE NEW CULTIVAR

The following detailed descriptions set forth the distinctive characteristics of 'Astra Snowwhite'. The data which defines these characteristics were collected from asexual reproductions carried out in Quedlinburg, Sachsen-Anhalt, Germany. Data was collected on plants propagated in the spring and the observations were made in October in the open field. Color references are primarily to the R.H.S. Colour Chart of The Royal Horticultural Society of London (R.H.S.) ($4^{th}$ ed).

DETAILED BOTANICAL DESCRIPTION

Classification:
- *Family.*—Compositae.
- *Botanical.*—*Osteospermum hybrida.*

Parentage:
- *Female parent.*—*Osteospermum* plant with white flowers.
- *Male parent.*—*Osteospermum* plant with cream flowers.

Plant:
- *Form and habit.*—Upright, bushy.
- *Growth and branching habit.*—Compact, upright growing with basal branching.
- *Height.*—30.0 cm to 50.0 cm.
- *Width.*—Radius: 15.0 cm to 25.0 cm. Diameter: 30.0 cm to 50.0 cm.
- *Propagation.*—Terminal tip cuttings.
- *Time to produce a finished flowering plant.*—10 to 12 weeks.
- *Time to initiate and develop roots.*—4 to 6 weeks.
- *Root description.*—Fine rooting system, with white to light brown roots.

Leaves:
- *Arrangement.*—Dextrorse or Sinistrorse.
- *Shape.*—Soft, but rough surface.

*Apex.*—Spiky.
*Base.*—Longish running to the stem.
*Margin.*—Weakly ridged.
*Immature leaf.*—General color: RHS 136B (Dark green). Upper surface: RHS 137B (Dark green). Lower surface: RHS 137C (Lighter green).
*Mature leaf.*—General color: RHS 139A (Dark green). Upper surface: RHS 137A (Dark green). Lower surface: RHS 137B (Lighter green).
*Length.*—4.0 cm to 5.5 cm.
*Width.*—1.0 cm to 2.5 cm.
*Texture.*—Rough.
*Petioles.*—Petioles winged by the leaf nearly direct to the branches.

Stems:
*Total number of branches.*—40 to 70.
*Length.*—30.0 cm to 50.0 cm.
*Diameter.*—Radius: 0.1 cm to 0.3 cm. Diameter: 0.2 cm to 0.6 cm.
*Internode length.*—1.0 cm to 3.5 cm.
*Color.*—RHS 137D (Light green with some anthocyanin).
*Texture.*—Smooth.

Inflorescence buds:
*Shape.*—Oval to longish.
*Length.*—0.5 cm to 1.0 cm.
*Diameter.*—Radius: 0.2 cm to 0.5 cm. Diameter: 0.4 cm to 1.0 cm.
*Color.*—RHS 137D (Light green).

Inflorescence:
*Type.*—Small flower (Astra) type.
*Blooming habit* (*flowering season*).—May to November.
*Quantity of inflorescences per plant.*—30 to 60.
*Lastingness of the inflorescences on the plant.*—About 7 days, but very much dependent on irrigation, fertilizer and temperature.
*Fragrance.*—Soft.
*Inflorescence diameter.*—Radius: 1.5 cm to 2.5 cm. Diameter: 3.0 cm to 5.0 cm.
*Disc diameter.*—Radius: 0.3 cm to 0.6 cm. Diameter: 0.6 cm to 1.2 cm.

Disc floret:
*Quantity per inflorescence.*—50 to 70.
*Shape.*—Tubular.
*Tube color* (*closed*).—RHS 92A (Violet getting darker to the tip), Lower part RHS 137C (Light green).
*Tube color* (*mature*).—RHS 92A (Violet getting darker to the tip), Lower part RHS 138A (Light green).
*Length.*—0.5 cm to 0.8 cm.
*Diameter* (*at apex*).—Radius: Less than 0.1 cm. Diameter: 0.1 cm.
*Apex.*—Relatively flat.
*Apex color.*—RHS 92A (Violet).
*Base.*—RHS 138D (Soft green).
*Margin.*—Fused until about 0.3 cm before apex.

Ray floret:
*Quantity per inflorescence.*—20.
*Shape.*—Longish to oval.
*Color.*—RHS 155D (White), at base RHS 92A (Violet). Upper surface: RHS 155D (White). Lower surface: RHS 92A (Violet striped).
*Length.*—1.5 cm to 2.0 cm.
*Width.*—0.3 to 0.7 cm.
*Apex.*—Nearly round, a little bit ridged.
*Base.*—Fused.
*Margin.*—Entire.
*Texture.*—Smooth.
*Peduncle.*—Length: 1.0 cm to 1.5 cm. Diameter: Radius: 1.5 cm to 2.5 cm. Diameter: 3.0 cm to 5.0 cm. Texture: Soft. Color: RHS 155D to RHS 83C (White to purple).

Phyllaries:
*Arrangement.*—Not fused.
*Quantity.*—16.
*Shape.*—Longish.
*Color.*—RHS 138C (Light green). Upper surface: RHS 138C (Light green). Lower surface: RHS 138B (Darker green).
*Length.*—0.5 cm to 1.0 cm.
*Width.*—0.1 cm to 0.3 cm.
*Apex.*—Very spiky.
*Base.*—Running broad into the flower base.
*Margin.*—Lower part nearly transparent, at the tip RHS 138B (Green).
*Texture.*—Rough, pubescent.

Reproductive organs:
*Androecium.*—Location: Ray florets and Disc florets. Stamens: Quantity: 5. Shape: Longish. Color: RHS 83A (Dark purple). Filament length: 0.2 cm to 0.3 cm. Filament diameter: Radius: Less than 0.1 cm. Diameter: Less than 0.1 cm. Anther: Shape: Longish. Color: RHS 83A (Dark purple). Length: 0.1 cm to 0.3 cm. Diameter: Radius: Less than 0.1 cm. Diameter: Less than 0.1 cm. Pollen: Color: RHS 25A (Bright-orange). Amount: Moderate.
*Gynoecium.*—Location: Disc florets. Pistils: Number: 1. Length: 0.5 cm to 0.8 cm. Diameter: Radius: Less than 0.1 cm. Diameter: Less than 0.1 cm. Stigma: Color: RHS 92A (Violet). Shape: Round. Length: Less than 0.1 cm. Diameter: Radius: Less than 0.1 cm. Diameter: Less than 0.1 cm. Style: Color: RHS 155C (Nearly white). Length: 0.5 cm to 0.7 cm. Diameter: Radius: Less than 0.1 cm. Diameter: Less than 0.1 cm. Shape: Cylindrical.

Seeds:
*Color.*—RHS 165A (Brown).
*Length.*—0.4 cm to 0.7 cm.
*Diameter.*—Radius: 0.1 cm to 0.2 cm. Diameter: 0.2 cm to 0.4 cm.
*Shape.*—Triangular to flat.

Disease and insect resistance: Resistance and susceptibility is typical of the species.

COMPARISON WITH KNOWN CULTIVARS

'Astra Snowwhite' differs from the female parent plant in that the female parent is larger and has fewer flowers than 'Astra Snowwhite'.

'Astra Snowwhite' differs from the male parent plant in that the male parent has fewer flowers than 'Astra Snowwhite'. Additionally, 'Astra Snowwhite' has a white flower color, while the male parent has a cream flower color.

'Astra Snowwhite' differs from commercial *Osteospermum* variety 'Brightside' (U.S. Plant Pat. No. 10,596) in that 'Astra Snowwhite' has a more compact growth habit and smaller leaves. Additionally, 'Astra Snowwhite' has smaller flowers than that of 'Brightside'.

I claim:

1. A new and distinct cultivar of *Osteospermum* plant as described and shown herein.

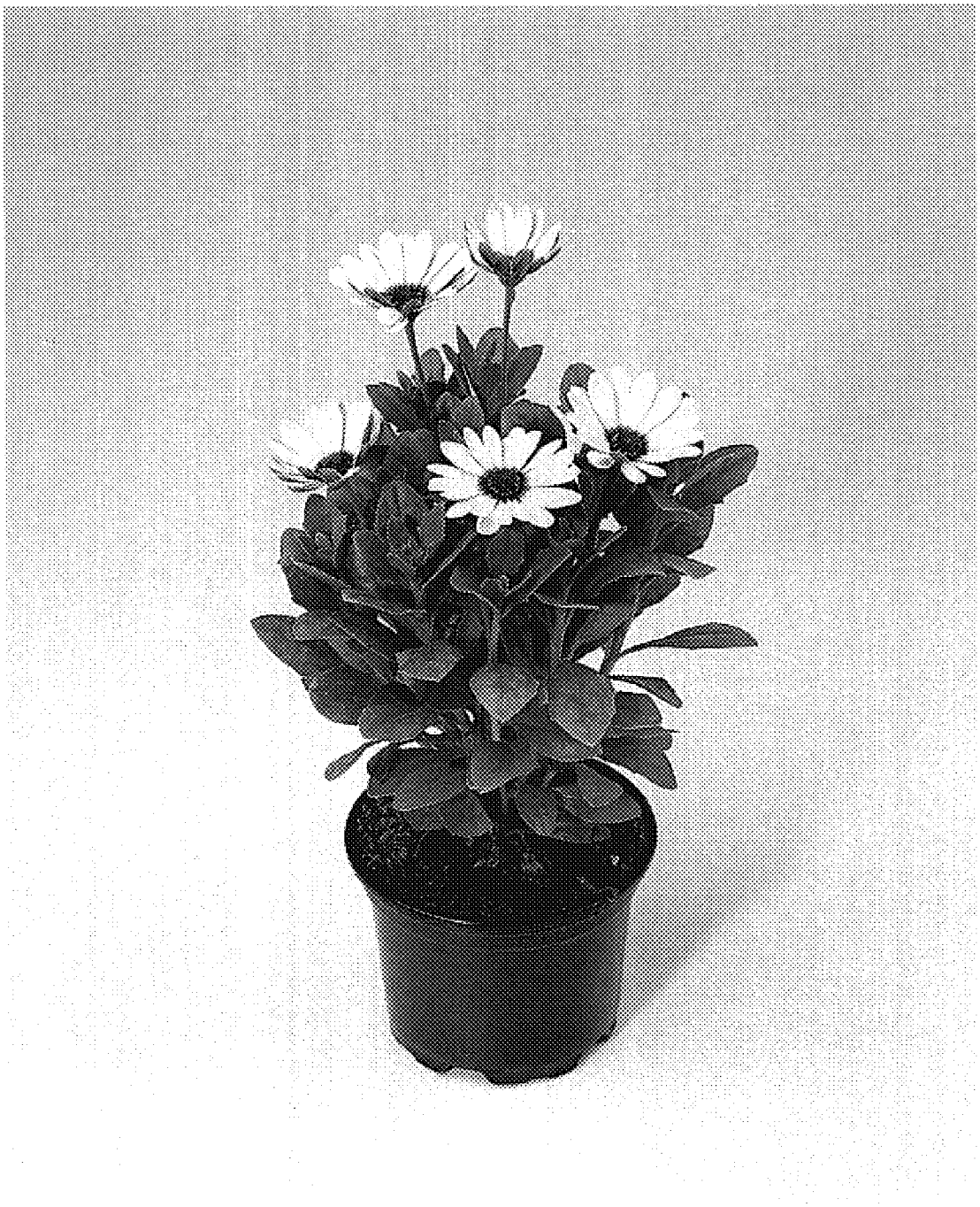

* * * * *